US009555154B2

(12) United States Patent
Belcheva et al.

(10) Patent No.: US 9,555,154 B2
(45) Date of Patent: Jan. 31, 2017

(54) MEDICAL DEVICES HAVING ACTIVATED SURFACES

(75) Inventors: Nadya Belcheva, Hamden, CT (US);
Ferass Abuzaina, Shelton, CT (US);
Amin Elachchabi, Hamden, CT (US);
Mbiya Kapiamba, Cromwell, CT (US);
Ahmed Robert Hadba, Middlefield, CT (US)

(73) Assignee: Covidien LP, Mansfield, MA (US)

( * ) Notice: Subject to any disclaimer, the term of this patent is extended or adjusted under 35 U.S.C. 154(b) by 976 days.

(21) Appl. No.: 13/202,357

(22) PCT Filed: Feb. 19, 2010

(86) PCT No.: PCT/US2010/024727
§ 371 (c)(1),
(2), (4) Date: Nov. 3, 2011

(87) PCT Pub. No.: WO2010/096649
PCT Pub. Date: Aug. 26, 2010

(65) Prior Publication Data
US 2012/0041546 A1 Feb. 16, 2012

Related U.S. Application Data

(60) Provisional application No. 61/154,375, filed on Feb. 21, 2009.

(51) Int. Cl.
| | |
|---|---|
| *A61F 2/06* | (2013.01) |
| *B32B 9/04* | (2006.01) |
| *B32B 27/40* | (2006.01) |
| *B05D 7/00* | (2006.01) |
| *B32B 27/00* | (2006.01) |
| *B05D 3/10* | (2006.01) |
| *B32B 27/34* | (2006.01) |
| *A61L 17/10* | (2006.01) |
| *A61L 17/12* | (2006.01) |
| *C08J 7/12* | (2006.01) |

(52) U.S. Cl.
CPC .......... *A61L 17/10* (2013.01); *A61L 17/12* (2013.01); *C08J 7/123* (2013.01); *Y10T 428/3154* (2015.04); *Y10T 428/31504* (2015.04); *Y10T 428/31551* (2015.04); *Y10T 428/31663* (2015.04); *Y10T 428/31725* (2015.04); *Y10T 428/31855* (2015.04)

(58) Field of Classification Search
CPC ........... C08F 8/26; C08F 110/10; C08F 8/12; C08F 8/00; C08F 8/30; C08F 138/00; C08F 8/22; C08F 2438/01; C08F 293/005; C08F 8/04; C08F 238/00; C08F 283/00; C08F 293/00; C08F 2/38; C08F 8/02
See application file for complete search history.

(56) References Cited

U.S. PATENT DOCUMENTS

| | | |
|---|---|---|
| 3,767,085 A | 10/1973 | Cannon et al. |
| 4,326,532 A | 4/1982 | Hammar |
| 4,359,049 A | 11/1982 | Redl et al. |
| 4,464,321 A | 8/1984 | Pittalis et al. |
| 4,538,920 A | 9/1985 | Drake |
| 4,753,536 A | 6/1988 | Spehar et al. |
| 4,839,345 A | 6/1989 | Doi et al. |
| 4,857,403 A | 8/1989 | De Lucca et al. |
| 4,880,662 A | 11/1989 | Habrich et al. |
| 5,021,207 A | 6/1991 | De Lucca et al. |
| 5,372,585 A | 12/1994 | Tiefenbrun et al. |
| 5,455,308 A | 10/1995 | Bastiaansen |
| 5,562,946 A | 10/1996 | Fofonoff et al. |
| 5,578,662 A | 11/1996 | Bennett et al. |
| 5,582,955 A | 12/1996 | Keana et al. |
| 5,612,050 A | 3/1997 | Rowe et al. |
| 5,804,318 A | 9/1998 | Pinchuk et al. |
| 5,911,942 A | 6/1999 | Fofonoff et al. |
| 6,099,563 A | 8/2000 | Zhong |
| 6,107,365 A | 8/2000 | Bertozzi et al. |
| 6,107,453 A | 8/2000 | Zuccato et al. |
| 6,312,725 B1 | 11/2001 | Wallace et al. |
| 6,342,591 B1 | 1/2002 | Zamora et al. |
| 6,451,032 B1 | 9/2002 | Ory et al. |
| 6,534,611 B1 | 3/2003 | Darling et al. |
| 6,552,103 B1 | 4/2003 | Bertozzi et al. |
| 6,570,040 B2 | 5/2003 | Saxon et al. |
| 6,576,000 B2 | 6/2003 | Carrison |
| 6,624,245 B2 | 9/2003 | Wallace et al. |
| 6,881,766 B2 | 4/2005 | Hain |
| 6,958,212 B1 | 10/2005 | Hubbell et al. |
| 7,012,126 B2 | 3/2006 | Matsuda et al. |
| 7,105,629 B2 | 9/2006 | Matsuda et al. |
| 7,122,703 B2 | 10/2006 | Saxon et al. |
| 7,144,976 B2 | 12/2006 | Matsuda et al. |
| 7,172,877 B2 | 2/2007 | Ting |
| 7,201,935 B1 * | 4/2007 | Claude et al. ............... 427/2.1 |
| 7,247,692 B2 | 7/2007 | Laredo |
| 7,294,357 B2 | 11/2007 | Roby |
| 7,371,719 B2 | 5/2008 | Stupp et al. |

(Continued)

FOREIGN PATENT DOCUMENTS

| | | |
|---|---|---|
| BE | 1008260 A6 | 2/1996 |
| DE | 10106230 A1 | 8/2002 |

(Continued)

OTHER PUBLICATIONS

Q. Shi, et al., "The Immobilization of Proteins on Biodegradable Polymer Fibers via Click Chemistry", Biomaterials, 29, (2008), pp. 1118-1126.

Jérôme, et al., "Recent Advances in the Synthesis of Aliphatic Polyesters Ring-Opening Polymerization", Advanced Drug Delivery Reviews, 60, (2008), pp. 1056-1076.

Zhang, et al., "2-Azido-2-deoxycellulose: Synthesis and 1, 3-Dipolar Cycloaddition", Helvetica Chimica Acta, vol. 91, pp. 608-617 (2008).

(Continued)

*Primary Examiner* — Audrea Buckley

(57) ABSTRACT

Implantable biocompatible polymeric medical devices include a substrate with a plasma-modified surface which is subsequently modified to include click reactive members.

22 Claims, 1 Drawing Sheet

(56) References Cited

U.S. PATENT DOCUMENTS

| | | |
|---|---|---|
| 7,375,234 B2 | 5/2008 | Sharpless et al. |
| 7,560,588 B2 | 7/2009 | Breitenkamp et al. |
| 7,618,944 B2 | 11/2009 | Breitenkamp et al. |
| 7,638,558 B2 | 12/2009 | Breitenkamp et al. |
| 7,667,012 B2 | 2/2010 | Saxon et al. |
| 7,795,355 B2 | 9/2010 | Matyjaszewski et al. |
| 7,807,619 B2 | 10/2010 | Bertozzi et al. |
| 7,981,444 B2 | 7/2011 | Tomalia et al. |
| 7,985,424 B2 | 7/2011 | Tomalia et al. |
| 8,034,396 B2 | 10/2011 | Kapiamba et al. |
| 2002/0016003 A1 | 2/2002 | Saxon et al. |
| 2002/0161170 A1 | 10/2002 | Matsuda et al. |
| 2002/0169275 A1 | 11/2002 | Matsuda et al. |
| 2002/0173616 A1 | 11/2002 | Matsuda et al. |
| 2003/0100086 A1 | 5/2003 | Yao et al. |
| 2003/0135238 A1 | 7/2003 | Milbocker |
| 2003/0162903 A1 | 8/2003 | Day |
| 2003/0199084 A1 | 10/2003 | Saxon et al. |
| 2003/0205454 A1 | 11/2003 | Hlavinka et al. |
| 2004/0170752 A1 | 9/2004 | Luthra et al. |
| 2004/0185053 A1 | 9/2004 | Govindan |
| 2004/0209317 A1 | 10/2004 | Ting |
| 2004/0249438 A1 | 12/2004 | Lefranc et al. |
| 2005/0032081 A1 | 2/2005 | Ju et al. |
| 2005/0038472 A1 | 2/2005 | Furst |
| 2005/0148032 A1 | 7/2005 | Saxon et al. |
| 2005/0222427 A1 | 10/2005 | Sharpless et al. |
| 2005/0233062 A1* | 10/2005 | Hossainy et al. ............. 427/2.1 |
| 2005/0233389 A1 | 10/2005 | Ting et al. |
| 2005/0244453 A1 | 11/2005 | Stucke et al. |
| 2006/0018948 A1 | 1/2006 | Guire et al. |
| 2006/0036022 A1 | 2/2006 | Callaghan et al. |
| 2006/0085033 A1 | 4/2006 | Criscuolo et al. |
| 2006/0108393 A1 | 5/2006 | Heinrich et al. |
| 2006/0110782 A1 | 5/2006 | Bertozzi et al. |
| 2006/0142404 A1 | 6/2006 | Berge et al. |
| 2006/0147963 A1 | 7/2006 | Barone et al. |
| 2006/0193865 A1 | 8/2006 | Govindan |
| 2006/0228300 A1 | 10/2006 | Chang et al. |
| 2006/0228357 A1 | 10/2006 | Chang et al. |
| 2006/0240092 A1 | 10/2006 | Breitenkamp et al. |
| 2006/0276658 A1 | 12/2006 | Saxon et al. |
| 2007/0020620 A1 | 1/2007 | Finn et al. |
| 2007/0037964 A1 | 2/2007 | Saxon et al. |
| 2007/0060658 A1 | 3/2007 | Diaz et al. |
| 2007/0077564 A1 | 4/2007 | Roitman et al. |
| 2007/0086942 A1 | 4/2007 | Chang et al. |
| 2007/0087001 A1 | 4/2007 | Taylor et al. |
| 2007/0099251 A1 | 5/2007 | Zhang et al. |
| 2007/0122540 A1 | 5/2007 | Salamone et al. |
| 2007/0140966 A1 | 6/2007 | Chang et al. |
| 2007/0178133 A1* | 8/2007 | Rolland ............. 424/423 |
| 2007/0178448 A1 | 8/2007 | Tsao et al. |
| 2007/0190597 A1 | 8/2007 | Agnew et al. |
| 2007/0212267 A1 | 9/2007 | Organ et al. |
| 2007/0244265 A1 | 10/2007 | Matyjaszewski et al. |
| 2007/0244296 A1 | 10/2007 | Tomalia et al. |
| 2007/0249014 A1 | 10/2007 | Agnew et al. |
| 2007/0254006 A1 | 11/2007 | Loose et al. |
| 2007/0258889 A1 | 11/2007 | Douglas et al. |
| 2007/0269369 A1 | 11/2007 | Gegg et al. |
| 2007/0272122 A1 | 11/2007 | Lahann et al. |
| 2007/0275387 A1 | 11/2007 | Ju |
| 2007/0298006 A1 | 12/2007 | Tomalia et al. |
| 2008/0015138 A1 | 1/2008 | Hamilton et al. |
| 2008/0021486 A1 | 1/2008 | Oyola et al. |
| 2008/0035243 A1* | 2/2008 | Breitenkamp et al. ....... 148/240 |
| 2008/0038472 A1 | 2/2008 | Suzuki et al. |
| 2008/0045686 A1 | 2/2008 | Meagher et al. |
| 2008/0050731 A1 | 2/2008 | Agnew et al. |
| 2008/0051562 A1 | 2/2008 | Chaikof et al. |
| 2008/0103564 A1 | 5/2008 | Burkinshaw et al. |
| 2008/0121657 A1 | 5/2008 | Voegele et al. |
| 2008/0138317 A1 | 6/2008 | Fung |
| 2008/0160017 A1 | 7/2008 | Baker et al. |
| 2008/0166363 A1 | 7/2008 | Govindan et al. |
| 2008/0171067 A1 | 7/2008 | Govindan et al. |
| 2008/0187956 A1 | 8/2008 | Carrico et al. |
| 2008/0199736 A1 | 8/2008 | Gadeken et al. |
| 2008/0200628 A1 | 8/2008 | Gadeken et al. |
| 2008/0207913 A1 | 8/2008 | Breitenkamp et al. |
| 2008/0214436 A1 | 9/2008 | Yu et al. |
| 2008/0214801 A1 | 9/2008 | Saxon et al. |
| 2008/0214831 A1 | 9/2008 | Sharpless et al. |
| 2008/0221043 A1 | 9/2008 | Harth et al. |
| 2008/0241856 A1 | 10/2008 | Wong et al. |
| 2008/0241892 A1 | 10/2008 | Roitman et al. |
| 2008/0242171 A1 | 10/2008 | Huang et al. |
| 2008/0248126 A1 | 10/2008 | Cheng et al. |
| 2008/0267878 A1 | 10/2008 | Robillard et al. |
| 2008/0283572 A1 | 11/2008 | Boyden et al. |
| 2008/0311412 A1 | 12/2008 | Fokin et al. |
| 2008/0317861 A1 | 12/2008 | Guan |
| 2009/0012457 A1 | 1/2009 | Childers et al. |
| 2009/0018646 A1* | 1/2009 | Zhao ............. 623/1.43 |
| 2009/0027603 A1 | 1/2009 | Samulski et al. |
| 2009/0038701 A1 | 2/2009 | Delmotte |
| 2009/0053139 A1 | 2/2009 | Shi et al. |
| 2009/0054619 A1 | 2/2009 | Baker et al. |
| 2009/0061010 A1 | 3/2009 | Zale et al. |
| 2009/0069561 A1 | 3/2009 | Fokin et al. |
| 2009/0082224 A1 | 3/2009 | Haddleton et al. |
| 2009/0099108 A1 | 4/2009 | Jones |
| 2009/0124534 A1 | 5/2009 | Reineke et al. |
| 2009/0137424 A1 | 5/2009 | Tsao et al. |
| 2009/0181402 A1 | 7/2009 | Finn et al. |
| 2009/0182151 A1 | 7/2009 | Wu et al. |
| 2009/0202433 A1 | 8/2009 | Chang et al. |
| 2009/0203131 A1 | 8/2009 | Reineke et al. |
| 2009/0214755 A1 | 8/2009 | Armani et al. |
| 2009/0220607 A1 | 9/2009 | Kiser et al. |
| 2009/0240030 A1 | 9/2009 | Ju et al. |
| 2009/0247651 A1 | 10/2009 | Kapiamba et al. |
| 2009/0250588 A1 | 10/2009 | Robeson et al. |
| 2009/0253609 A1 | 10/2009 | Fleury et al. |
| 2009/0259016 A1 | 10/2009 | Johnson et al. |
| 2009/0263468 A1 | 10/2009 | McAnulty et al. |
| 2009/0269277 A1 | 10/2009 | Chang et al. |
| 2009/0281250 A1 | 11/2009 | DeSimone et al. |
| 2009/0297609 A1 | 12/2009 | Shoichet et al. |
| 2009/0306310 A1 | 12/2009 | Wu et al. |
| 2009/0312363 A1 | 12/2009 | Bradner et al. |
| 2009/0325292 A1 | 12/2009 | Baker et al. |
| 2010/0011472 A1 | 1/2010 | Hugel et al. |
| 2010/0015046 A1 | 1/2010 | Govindan et al. |
| 2010/0021391 A1 | 1/2010 | Douglas et al. |
| 2010/0034862 A1 | 2/2010 | Laronde et al. |
| 2010/0047258 A1 | 2/2010 | Wang et al. |
| 2010/0048738 A1 | 2/2010 | Fleury et al. |
| 2010/0069578 A1 | 3/2010 | Faust et al. |
| 2010/0098640 A1 | 4/2010 | Cohen et al. |
| 2010/0104589 A1 | 4/2010 | Govindan et al. |
| 2010/0121022 A1 | 5/2010 | Musa et al. |
| 2010/0159508 A1 | 6/2010 | Yang et al. |
| 2010/0247433 A1 | 9/2010 | Tirrell et al. |
| 2010/0286405 A1 | 11/2010 | Fokin et al. |
| 2010/0291171 A1 | 11/2010 | Crescenzi et al. |
| 2010/0303754 A1 | 12/2010 | Turpin et al. |
| 2011/0008251 A1 | 1/2011 | Chang et al. |
| 2011/0052696 A1 | 3/2011 | Hult et al. |
| 2011/0060107 A1 | 3/2011 | Matyjaszewski et al. |
| 2011/0143435 A1 | 6/2011 | Stayton et al. |
| 2011/0177156 A1 | 7/2011 | Szoka, Jr. et al. |
| 2011/0183417 A1 | 7/2011 | Reineke |
| 2011/0213123 A1 | 9/2011 | Bertozzi et al. |

FOREIGN PATENT DOCUMENTS

| | | |
|---|---|---|
| EP | 0490854 B1 | 9/1996 |
| EP | 1790702 A1 | 5/2007 |
| EP | 1795563 A1 | 6/2007 |
| EP | 1975230 A1 | 1/2008 |
| EP | 2014308 A2 | 1/2009 |
| EP | 2090592 A1 | 8/2009 |

(56) References Cited

FOREIGN PATENT DOCUMENTS

| WO | WO 2006/012569 A1 | 2/2006 |
|---|---|---|
| WO | WO 2007/041394 A2 | 4/2007 |
| WO | WO 2007/121055 A1 | 10/2007 |
| WO | 2008005752 A2 | 1/2008 |
| WO | WO 2008/013618 A1 | 1/2008 |
| WO | WO 2008/075955 A2 | 6/2008 |
| WO | WO 2008/077406 A2 | 7/2008 |
| WO | WO 2008/108736 A1 | 9/2008 |
| WO | WO 2008/115694 A2 | 9/2008 |
| WO | WO 2008/120016 A1 | 10/2008 |
| WO | WO 2010/095049 A1 | 8/2010 |

OTHER PUBLICATIONS

R. Riva, et al., "Contribution of "Click Chemistry" to the Synthesis of Antimicrobial Aliphatic Copolyester", Polymer 49, (2008), pp. 2023-2028.

Baskin, et al., "Copper Free Click Chemistry for Dynamic In Vivo Imaging", PNAS, vol. 104, No. 43, (Oct. 23, 2007), pp. 16793-16797.

Codelli, et al., "Second Generation Difluorinated Cyclooctynes for Copper-Free Click Chemistry", J. Am. Chem. Soc., vol. 130, No. 34, (2008), pp. 11486-11493.

Sletten and Bertozzi, "A Hydrophilic Azacyclooctyne for Cu-free Click Chemistry", Org. Lett. (2008) 10(14), pp. 3097-3099.

Cazalis, et al., "C-Terminal Site-Specific PEGylation of a Truncated Thrombomodulin Mutant with Retention of Full Bioactivity", Bioconjugate Chem., (2004), 15, pp. 1005-1009.

Haridas, et al., "Design and Synthesis of Triazole-based Peptidedendrimers" Tetrahedron Letters, vol. 48, (2007), pp. 4719-4722.

Raghavan, et al., "Chemical Probes for Profiling Fatty Acid-associated Proteins in Living Cells", Bioorg. Med. Chem. Lett., 18 (2008), pp. 5982-5986.

LeDévédec, et al., "Separation of Chitosan Oligomers by Immobilized Metal Affinity Chromatography", Journal of Chromatography A., 2008, 1194(2), pp. 165-171.

Hartgerink, et al., "Peptide-amphiphile Nanofibers: A Versatile Scaffold for the Preparation of Self Assembling Materials", PNAS, 2002; 99(2), pp. 5133-5138.

Van Berkel, et al., "Metal-Free Triazole Formation as a Tool for Bioconjugation" Chem Bio Chem, 8, (2007), pp. 1504-1508.

Nottelet, et al., Synthesis of an X-ray opaque biodegradable copolyester by chemical modification of poly (ε-caprolactone) Biomaterials, 27, (2006), pp. 4943-4954.

Smith, et al., "Synthesis and Convenient Functionalization of Azide-labeled Diacyglycerol Analogues for Modular Access to Biologically Active Lipid Probes", Bioconjugate Chem, 19(9), (2008). pp. 1855-1863.

Skierka, et al., "The Influence of Different Acids and Pepsin on the Extractability of Collagen From the Skin of Baltic Cod (*Gadus Morhua*)", Food Chemisty, 105, (2007), pp. 1302-1306.

Eastoe, "The Amino Acid Composition of Mammalian Collagen and Gelatin", vol. 61, (1955), pp. 589-600.

Sicherl, et al., "Orthogonally Protected Sugar Diamino Acids as Building Blocks for Linear and Branched Oligosaccharide Mimetics", Angew. Chem. Int. Ed. 44, (2005), pp. 2096-2099.

Laughlin, et al., "In Vivo Imaging of Membrane-Associated Glycans in Developing Zebrafish", Science, 320, (2008), pp. 664-667.

Worch and Wittmann, "Unexpected Formation of Complex Bridged Tetrazoles via Intramolecular 1,3-dipolar Cycloaddition of 1,2-0-cyanoalkylidene Derivatives of 3-azido-3-deoxy-D-allose", Carbohydrate Research, 343, (2008), pp. 2118-2129.

Witczak et al., "A Click Chemistry Approach to Glycomimetics: Michael addition of 2,3,4,6-tetra-*O*-acetyl-1-thio-β-D-glucopyranose to 4-deoxy-1,2-*O*-isopropylident-L-*glycero*-pent-4-enopyranos-3-ulose-a convenient route to novel 4-deoxy-(1→5)-5-*C*-thiodisaccharides", Carbohydrate Research, 342, (2007), 1929-1933.

Marra, et al., "Validation of the Copper(1)-Catalyzed Azide-Alkyne Coupling in Ionic Liquids, Synthesis of a Triazole-Linked C-Disaccharide as a Case Study", J. Org. Chem (2008), 73(6), pp. 2458-2461.

Srinivasachari, et al., "Versatile Supramolecular pDNA Vehicles via "Click Polymerization" of β-cyclodextrin with oligoethyleneamines", Biomaterials, 30, (2009), pp. 928-938.

Arora, et al., "A Novel domino-click approach for the synthesis of sugar based unsymmetrical bis-1,2,3-triazoles", Carbohydrate Research, 343, (2008), 139-144.

Chen, et al., "Synthesis of a $C_3$-symmetric (1→6)-*N*-acetyl-β-D-glucosamine Octadecasaccharide using Click Chemisty", Carbohydrate Research, 340, (2005), pp. 2476-2482.

Gouin, et al., "Multi-Mannosides Based on a Carbohydrate Scaffold: Synthesis, Force Field Development, Molecular Dynamics Studies, and Binding Affinities for Lectin Con A", J. Org. Chem., 2007, 72(24), pp. 9032-9045.

Srinivasachari, etal., "Effects of Trehalose Click Polymer Length on pDNA Complex Stability and Delivery Efficacy", Biomaterials, 28, (2007), pp. 2885-2898.

Godeau, et al., Lipid-Conjugated Oligonucleotides via "Click Chemistry" Efficiently Inhibit Hepatitis C Virus Translation, J. med. Chem., 2008, 51(15), pp. 2374-4376.

Zou et al., "Cu-free Cycloaddition for Identifying Catalytic Active Adenylation Domains of Nonribosomal Peptide Synthesis by phage display", Bioorganic & Medicinal Chemistry Letters, 18 (2008), pp. 5664-5667.

Cantel, et al., "Synthesis and Conformational Analysis of a Cyclic Peptide Obtained via *i* to *i*+4 Intramolecular Side-chain to Side-chain Azide-Alkyne 1,3-Dipolar Cycloaddition" J. Org. Chem., 2008, 73(15), pp. 5663-5614.

Dijk, et al., "Synthesis of Peptide-Based Polymers by Microwave-Assisted Cycloaddition Backbone Polymerization," Biomacro molecules, 2007, 8(2), pp. 327-330.

Köster, et al., "Spectroscopic and Electrochemical Studies of Ferroceryl Triazole Amino Acid and Peptide Bioconjugates Synthesized by Click Chemistry", Organometallics, 2008, 27(23) pp. 6326-6332.

Dijk, et al., "Synthesis and Characterization of Biodegradable Peptide-Baed Polymers Prepared by Microwave-Assisted Click Chemisty", Biomacromolecules, 2008, 9(10), pp. 2834-2843.

Jiang, et al., "Amphiphilic PEG/alkyl-grafted comb polylactides", J. Polymer Science Part B: Polymer Physics, 45(22), 2007, pp. 5227-5236.

Ochs, et al., "Low-Fouling, Biofunctionalized, and Biodegradable Click Capsules", Biomacromolecules, 2008, 9(12), pp. 3389-3396.

Beatty and Tirrell, "Two-color Labeling of Temporally Defined Protein Populations in Mammalian Cells", Bioorg. Med. Chem. Lett., 18 (2008), pp. 5995-5999.

Kolb, et al., "Click Chemistry: Diverse Chemical Function from a Few Good Reactions", Angewandte Chemie, International Edition, Jun. 2001, pp. 2004-2021.

Krouit, et al., "Cellulose surface grafting with polycaprolactone by heterogeneous click-chemistry", European Polymer Journal 44, Dec. 2008, pp. 4074-4081.

Nandivada, et al. "Reactive polymer coatings that 'Click'.", Angewandte Chemie, International Edition 45, Apr. 2006, pp. 3360-3363.

Ossipov and Hilborn, "Poly(vinyl alcohol)-Based Hydrogels Formed by Click Chemistry", Macromelecules 2006, 39, pp. 1709-1718.

Binder and Sachsenhofer, "Click Chemistry in Polymer and Materials Science", Macromolecular Rapid Commun. 2007, 28, pp. 15-54.

European Communication dated Nov. 27, 2015 in EP Patent Application No. 10744354.1, 7 pages.

European Search Report, Application No. EP 10 74 4354 dated Mar. 13, 2014.

(56) References Cited

OTHER PUBLICATIONS

European Examination Report issued in corresponding European Patent Application No. 10744354.1 on Oct. 18, 2016, 6 pages.

* cited by examiner

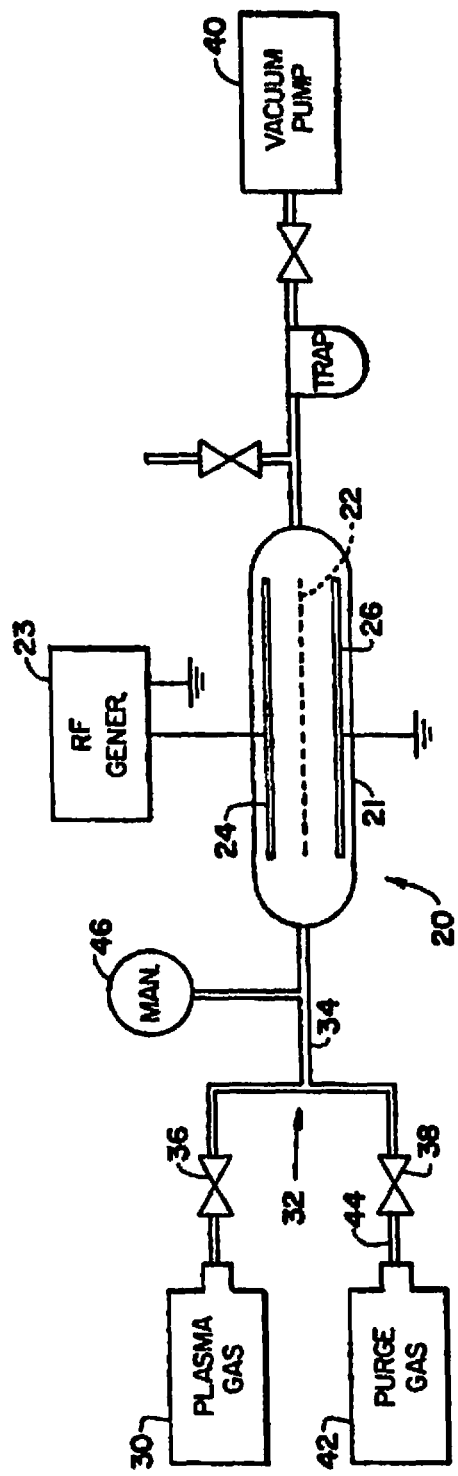

MEDICAL DEVICES HAVING ACTIVATED SURFACES

CROSS-REFERENCE TO RELATED APPLICATIONS

This application is a U.S. National Stage Application filed under 35 U.S.C. §371(a) of International Application No. PCT/US2010/024727 filed Feb. 19, 2010, which claims the benefit of and priority to U.S. Provisional Application Ser. No. 61/154,375 filed Feb. 21, 2009, the entire contents of which are incorporated by reference herein.

BACKGROUND

1. Technical Field

The present disclosure relates to medical devices having an activated surface.

2. Related Art

Biocompatible and biodegradable materials have been used for the manufacture of prosthetic implants, suture threads, and the like. A relative advantage of these materials is that of eliminating the need for a second surgical intervention to remove the implant. The gradual biodegradability of such materials favors regeneration of the pre-existing tissues. There has been recent interest in using such devices for delivery of bioactive agents.

It would be advantageous to provide reactive functional groups on the surface of such biodegradable medical devices for a variety of purposes.

SUMMARY

Implantable biocompatible polymeric medical devices in accordance with the present disclosure include a substrate with a plasma-modified surface which is subsequently modified to include click reactive members. The substrate of the medical devices described herein may be made from any biocompatible polymer and can be part of any medical device of being implanted at a target location. Plasma treatment of the substrate may result in chemical modification of the material from which the substrate is made or in the deposition of a coating of a linking material to which click reactive members may be covalently attached thereby.

BRIEF DESCRIPTION OF THE DRAWINGS

The accompanying drawings, which are incorporated in and constitute a part of this specification, illustrate embodiments of the disclosure and, together with a general description of the disclosure given above, and the detailed description of the embodiments given below, serve to explain the principles of the disclosure.

FIG. 1 is a schematic illustration of an apparatus which is suitable for carrying out plasma treatment of a substrate in accordance with the present disclosure.

DETAILED DESCRIPTION OF THE EMBODIMENTS

Implantable biocompatible polymeric medical devices in accordance with the present disclosure include a substrate with a plasma-modified surface which is subsequently modified to include click reactive members.

The Polymeric Substrate

The substrate of the medical devices described herein may be made from any biocompatible polymer. The biocompatible polymer may be a homopolymer or a copolymer, including random copolymer, block copolymer, or graft copolymer. The biocompatible polymer may be a linear polymer, a branched polymer, or a dendrimer. The biocompatible polymer may be bioabsorbable or non-absorbable and may be of natural or synthetic origin.

Examples of suitable biodegradable polymers from which the substrate of the medical devices described herein may be made include, but are not limited to polymers such as those made from lactide, glycolide, $\epsilon$-caprolactone, $\delta$-valerolactone, carbonates (e.g., trimethylene carbonate, tetramethylene carbonate, and the like), dioxanones (e.g., 1,4-dioxanone), 1,dioxepanones (e.g., 1,4-dioxepan-2-one and 1,5-dioxepan-2-one), ethylene glycol, ethylene oxide, esteramides, hydroxy alkanoates (e.g., $\gamma$-hydroxyvalerate, $\beta$-hydroxypropionate, hydroxybuterates), poly (ortho esters), tyrosine carbonates, polyimide carbonates, polyimino carbonates such as poly (bisphenol A-iminocarbonate) and poly (hydroquinone-iminocarbonate), polyurethanes, polyanhydrides, polymer drugs (e.g., polydiflunisol, polyaspirin, and protein therapeutics) and copolymers and combinations thereof. Suitable natural biodegradable polymers include collagen, cellulose, poly (amino acids), polysaccharides, hyaluronic acid, gut, copolymers and combinations thereof.

Examples of suitable non-degradable polymers from which the substrate of the medical devices described herein may be made include, but are not limited to fluorinated polymers (e.g. fluoroethylenes, propylenes, fluoroPEGs), polyolefins such as polyethylene, polyesters such as poly ethylene terephthalate (PET), nylons, polyamides, polyurethanes, silicones, ultra high molecular weight polyethylene (UHMWPE), polybutesters, polyaryletherketone, copolymers and combinations thereof.

The biocompatible polymeric substrate may be fabricated into any desired physical form. The polymeric substrate may be fabricated for example, by spinning, casting, molding or any other fabrication technique known to those skilled in the art. The polymeric substrate may be made into any shape, such as, for example, a fiber, sheet, rod, staple, clip, needle, tube, foam, or any other configuration suitable for a medical device. Where the polymeric substrate is in the form of a fiber, the fiber may be formed into a textile using any known technique including, but not limited to, knitting, weaving, tatting and the like. It is further contemplated that the polymeric substrate may be a non-woven fibrous structure.

The present biocompatible polymeric substrate can be part of any medical device of being implanted at a target location. Some non-limiting examples include monofilaments, multifilaments, surgical meshes, ligatures, sutures, staples, patches, slings, foams, pellicles, films, barriers, stents, catheters, shunts, grafts, coil, inflatable balloon, and the like. The implantable device can be intended for permanent or temporary implantation.

Plasma Treatment of the Substrate

Plasma treatment of the substrate may result in chemical modification of the material from which the substrate is made, thereby producing sites for the covalent attachment of click reactive members. Alternatively, plasma treatment may result in the deposition of a coating of a linking material to which click reactive members may be covalently attached.

The term "plasma" refers to a thermodynamically non-equilibrium gaseous complex, composed of electrons, ions, gas atoms, free radicals, and molecules in an excited state, known as the plasma state. Plasma may be generated in a process known as plasma discharge by a number of methods including combustion, flames, electric discharges, controlled nuclear reactions and shocks. The most commonly used is electric discharge.

An illustrative plasma treatment apparatus is shown in FIG. 1. Positioned in chamber 21 are rack 22, preferably made of stainless steel and a pair of parallel electrode plates 24 and 26 between which the plasma is formed. Radio frequency generator 23 is provided as a source of potential, the output terminal of generator 23 being connected to plate 24, plate 26 being grounded, thereby providing means for generating an electrical field between the plates, in which field a plasma can be created and sustained. To provide the desired gas from which the plasma is formed, the apparatus includes gas source 30 (typically a standard gas cylinder) connected through gas inlet system 32 to chamber 21. System 32 is typically formed of supply line 34 connected to source 30, valve 36 for controlling the flow of gas through line 34, and valve 38. The apparatus also includes vacuum pump 40 connected to chamber 21 for reducing the gas pressure therein. A source 42 of purge gas such as helium is connected through line 44 to valve 38 of valve system 32.

In a typical reaction, the substrate is mounted in chamber 21 on steel rack 22, the latter then being positioned between electrodes 24 and 26. Vacuum pump 40 is operated to reduce the pressure in chamber 21 to below 0.1 torr. Valve system 32 is operated to permit reacting gas monomer from source 30 to flow into chamber 21 through line 34 for approximately 10 minutes before generating a plasma.

The plasma is created by applying the output of radio frequency generator 23, operating typically at 13.56 MHz, to electrode plate 24. The power supplied by generator 23 is controlled at the minimum required to sustain the plasma, generally 50 to 100 watts. Higher powered plasma will only degrade the surface of the substrate. The reaction between the plasma and the substrate surface is allowed to proceed for a period of time determined by the desired thickness and surface energy on the substrates and the concentration of gas monomers in the reacting vapor. Typical reaction times are 15 seconds to 60 minutes. The thickness of the treated surface layer of the substrate should be between about 100 to 1500 Angstroms, in embodiments between about 200 and 1000 Angstroms. The pressure in chamber 21, as measured by capacitance nanometers 46 coupled to chamber 21 is maintained at 50 millitorrs throughout the reaction period.

Finally, all flow of gas from source 30 is terminated, the power from generator 23 sustaining the plasma is turned off, and valve 38 is opened to permit purge gas to flow into chamber 21 from source 42 to purge the substrate surface of highly reactive radicals which could cause premature contamination of the substrate surface. Valve 38 is then closed, the door to reactor chamber 21 is opened so that chamber 21 is returned to atmospheric pressure, and the plasma treated substrate is removed.

In embodiments, the substrate is made from a bioabsorbable polyester which, when plasma treated, contains reactive members. Plasma treatment of bioabsorbable polyester substrates can be carried out both in the presence of a reactive gas, for example air, Ar, $O_2$ with the formation of surface activation of oxygenate type, such as —OH, —CHO, —COOH.

In other embodiments, the plasma is produced using a nitrogen-containing molecule, an oxygen-containing molecule or mixtures thereof. In embodiments, mixtures of oxygen plus any one of ammonia, nitrous oxide (dinitrogen oxide), nitrogen dioxide, nitrogen tetroxide, ammonium hydroxide, nitrous acid, mixtures thereof, or sequential use of two or more of the materials within a plasma. Ozone may also be used in place of oxygen. It is also contemplated that mixtures of oxygen and nitrogen can be used. When a gas mixture is used, the ratio of the component gases may be varied to obtain an optimal concentration of each gas. Also, the gases may be used serially. For example, ammonia plasma may be generated first, followed by a plasma of oxygen. Typically, the plasma treatment is for less than about five minutes, in embodiments for less than about two minutes, in other embodiments for less than about one minute, and in yet other embodiments for between about thirty seconds and about one minute.

In embodiments, the substrate is treated with a plasma that utilizes a reactant gas mixture of ammonia and oxygen (hereafter an $NH_3/O_2$ plasma) at a plasma treatment temperature of less than 100° C., and, in embodiments, at ambient temperature. The reactant gas mixture is introduced into the plasma chamber through a gas inlet manifold. The gas inlet manifold may also be an electrode. The gas inlet manifold is one plate of a parallel plate plasma chamber for introducing the gas mixture into the chamber. The plate has a plurality of apertures, each comprising an outlet at a chamber or processing side of the plate and an inlet spaced from the processing side, with the entire plate complex being removable for ease of cleaning. The gas inlet manifold enhances the mixing of the gases.

In embodiments, the plasma treatment is of a plasma wherein the nitrogen-containing molecules are $NH_3$ and the oxygen-containing molecules are $O_2$. The mass flow rate during plasma treatment with each of $NH_3$ and of $O_2$ is between a ratio of about 1.5:1 and about 1:1.5. In alternative embodiments, the plasma treatment is of a plasma wherein the nitrogen-containing molecules are $N_2O$ and the oxygen-containing molecules are $O_2$. The mass flow rate during plasma treatment with each of $N_2O$ and of $O_2$ is between a ratio of about 1.5:1 and about 1:1.5.

In other embodiments, the substrate is treated in accordance with the present disclosure are subjected to a plasma polymerization process to form a polymer coating on at least a portion of the surface of the substrate. Plasma coating methods are disclosed, for example in U.S. Pat. No. 7,294,357, the entire disclosure of which is incorporated herein by this reference.

The monomers used to form the polymer coating are polymerized directly on the substrate surface using plasma-state polymerization techniques generally known to those skilled in the art. See, Yasuda, Plasma Polymerization, Academic Press Inc., New York (1985), the entire disclosure of which is incorporated herein by reference.

In brief, the monomers are polymerized onto the suture surface by activating the monomer in a plasma state. The plasma state generates highly reactive species, which form the characteristically highly cross-linked and highly-branched, ultra-thin polymer coating, which is deposited on the suture surface as it moves through the area of the reactor having the most intense energy density, known as the plasma glow zone.

For plasma polymerization to produce a coating on a substrate, which may also be called "plasma grafting", a suitable organic monomer or a mixture of monomers having polymerizable unsaturated groups is introduced into the plasma glow zone of the reactor where it is fragmented and/or activated forming further excited species in addition to the complex mixture of the activated plasma gases. The excited species and fragments of the monomer recombine upon contact with the substrate surface to form a largely undefined structure which contains a complex variety of different groups and chemical bonds and forms a highly cross-linked polymer coating on the suture surface. If $O_2$, $N_2$, or oxygen or nitrogen containing molecules are present, either within the plasma reactor during the polymer coating process, or on exposure of the polymer coated suture to oxygen or air subsequent to the plasma process, the polymeric deposit will include a variety of polar groups.

The amount and relative position of polymer deposition on the substrates are influenced by at least three geometric factors: (1) location of the electrodes and distribution of charge; (2) monomer flow; and (3) substrate position within the reactor relative to the glow region. In the case of substrates which can be pulled continuously through the plasma chamber (e.g., suture fibers), the influence of the suture position is averaged over the length of the fibers.

In practice, an electric discharge from an RF generator is applied to the "hot" electrodes of a plasma reactor. The selected monomers are introduced into the reactor and energized into a plasma, saturating the plasma glow zone with an abundance of energetic free radicals and lesser amounts of ions and free electrons produced by the monomers. As the substrate passes through or remains in the plasma glow zone, the surface of the substrate is continually bombarded with free radicals, resulting in the formation of the polymer coating.

In embodiments, the plasma chamber used for plasma polymerization has capacitively coupled plate-type electrodes. The substrate is exposed to monomers having a mass flow rate of from about 50 to about 100 standard cubic centimeters per minute (sccm), at an absolute pressure of from about 40 mTorr to about 70 mTorr. The exposure time can be from about 45 seconds to about 9 minutes, in embodiments from about 2 minutes to about 6 minutes. A radio frequency of 13.56 MHz with from about 25 watts to about 100 watts generates sufficient energy to activate the monomers.

It will be appreciated by those skilled in the art that in a differently configured plasma chamber, the monomer flow rate, power, chamber pressure, and exposure time may be outside the ranges of that set forth for the embodiment discussed above.

In embodiments, siloxane monomers are used in the plasma polymerization process to produce polymer coatings on the substrate surfaces. One preferred polymer coating which can be deposited on the substrate surface through the plasma state polymerization process of the present disclosure uses aliphatic hydrocyclosiloxane monomers of the general formula:

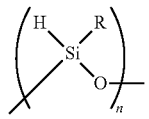

where R is an aliphatic group and n is an integer from 2 to about 10, in embodiments 4 to 6.

Examples of suitable aliphatic hydrocyclosiloxane monomers include: 1,3,5,7-tetramethylhydrocycltetrasiloxane ("TMCTS"); 1,3,5,7,9-pentamethylhydrocyclo pentasiloxane ("PMCTS"); 1,3,5,7,9,11-hexamethylhydrocyclohexasiloxane ("HMCHS") and a mixture of 1,3,5,7,9-pentamethylcyclosiloxane and 1,3,5,6,9,11-hexamethylcyclohexasiloxane monomers ("XMCXS").

The aliphatic hydrocyclosiloxane monomers noted above may be used to create a homogeneous coating on the substrate surface. In embodiments, the aliphatic hydrocyclosiloxane monomers may be mixed with co-monomers to give polymer coatings having properties different from the properties of the homogenous coating. For example, by introducing reactive functionalizing monomers, or organo-based monomers, or fluorocarbon monomers together with the aliphatic hydrocyclosiloxane monomers in the plasma polymerization system, physical pore size and chemical affinity of the plasma copolymerized aliphatic hydrocyclosiloxane coating with selective monomers can be controlled. This allows the use of the copolymerized plasma polymer coating for applications which require the coating to differentiate between certain types of gases, ions, and molecules and it also may be utilized to introduce functional groups to the polymer coating which, in turn, can help link other compounds or compositions to the polymer coating.

In embodiments, the polymer coatings may be produced by a plasma co-polymerization process of mixtures of the same aliphatic hydrocyclosiloxane monomers noted above with organo-based monomers that introduce amine groups onto the polymer coating and form amine grafted polymer coatings. These organo-based monomers can be introduced onto the polymer coating in a second plasma grafting process which occurs after the plasma polymerization of the aliphatic hydrocyclosiloxane monomers. Suitable organo-based monomers include allylamine, N-trimethylsilylallylamine, unsaturated amines (both N-protected and N-unprotected), and cyclic aliphatic amines (both N-protected and N-unprotected). As used herein, the term "amine grafted polymer coatings" refers to a polymer coating containing amine groups, which can be obtained either by co-polymerization of the organo-based monomer with the hydrocyclosiloxane monomer or by plasma grafting the organo-based monomer onto a previously formed siloxane polymer coating.

In yet another embodiment, these plasma treated substrates, possessing amine grafted polymer coatings, are then reacted with carbonate-based polyoxyalkylene compounds to produce polyoxyalkylene modified polymer coatings. In a preferred embodiment, the carbonate-based polyalkylene oxide is of the general formula:

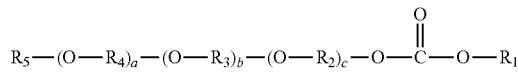

wherein $R_1$ is an N-benzotriazole group, an N-2-pyrrolidinone group, or a 2-oxypyrimidine group; $R_2$, $R_3$ and $R_4$ are independently selected alkylene groups of about 2 to about 3 carbon atoms and may be the same or different; $R_5$ is selected from hydrogen, methyl, a carbonyloxy-N-benzotriazole group, a carbonyloxy-N-2-pyrrolidinone group, and a carbonyl-2-oxypyrimidine group; a is an integer from 1 to 1000 and each of b and c is an integer from 0 to 1000, where a+b+c is an integer from 3 to 1000. Suitable lower alkylene groups include those having about 2 to about 3 carbon atoms.

In embodiments, compounds of the above formula, $R_2$, $R_3$ and $R_4$ is —($CH_2CH_2$)— or —$CH_2CH(CH_3)$— or any combination thereof. In embodiments, $R_2$, $R_3$ and $R_4$ are ethylene. According to certain embodiments a, b, and c are selected so as to give a molecular weight for the PEG moiety of about 500 to about 20,000, in embodiments from 3000 to 4000. Suitable polyoxyalkylene carbonates include, but are not limited to, polyoxyethylene bis-(2-hydroxypyrimidyl)

carbonate, polyoxyethylene bis-(N-hydroxybenzotriazolyl) carbonate and polyoxyethylene bis-(N-hydroxy-2-pyrrolidinonyl) carbonate.

These polyoxyalkylene modified polymer coatings possess a polyoxyalkylene tether capable being functionalized with a click reactive functional group as described hereinbelow.

The resulting coating on the substrate can be between about 0.01 to about 10 percent by weight based upon the weight of the substrate to which the coating is applied. In embodiments, the coating is applied in an amount of from about 0.05 to about 7.5 weight percent, in other embodiments, the amount of coating is between about 0.1 and about 5 weight percent. The amount of coating applied to the substrate may be adequate to coat all surfaces of the substrate. The term coating as used herein is intended to embrace both full and partial coatings.

The amount of coating composition may be varied depending on the construction of the substrate. In embodiments, the depth of cross-linking of the silicone coating with the surface of the suture is less than about 100 Å. The coatings may optionally contain other materials including colorants, such as pigments or dyes, fillers or therapeutic agents, such as antibiotics, growth factors, antimicrobials, wound-healing agents, etc. Depending on the amount of coating present, these optional ingredients may constitute up to about 25 percent by weight of the coating.

Addition of Reactive Members to the Plasma Treated Substrate

Once a surface of the substrate is plasma treated (either to provide active sites or a coating of a material containing active sites), click reactive functional groups are provided on the surface.

Click chemistry refers to a collection of reactive members having a high chemical potential energy capable of producing highly selective, high yield reactions. The reactive members react to form extremely reliable molecular connections in most solvents, including physiologic fluids, and often do not interfere with other reagents and reactions. Examples of click chemistry reactions include Huisgen cycloaddition, Diels-Alder reactions, thiol-alkene reactions, and maleimide-thiol reactions.

Huisgen cycloaddition is the reaction of a dipolarophile with a 1,3-dipolar compound that leads to 5-membered (hetero)cycles. Examples of dipolarophiles are alkenes and alkynes and molecules that possess related heteroatom functional groups (such as carbonyls and nitriles). 1,3-Dipolar compounds contain one or more heteroatoms and can be described as having at least one mesomeric structure that represents a charged dipole. They include nitril oxides, azides, and diazoalkanes. Metal catalyzed click chemistry is an extremely efficient variant of the Huisgen 1,3-dipolar cycloaddition reaction between alkyl-aryl-sulfonyl azides, C—N triple bonds and C—C triple bonds which is well-suited herein. The results of these reactions are 1,2 oxazoles, 1,2,3 triazoles or tetrazoles. For example, 1,2,3 triazoles are formed by a copper catalyzed Huisgen reaction between alkynes and alkly/laryl azides. Metal catalyzed Huisgen reactions proceed at ambient temperature, are not sensitive to solvents, i.e., nonpolar, polar, semipolar, and are highly tolerant of functional groups. Non-metal Huisgen reactions (also referred to as strain promoted cycloaddition) involving use of a substituted cyclooctyne, which possesses ring strain and electron-withdrawing substituents such as fluorine, that together promote a [3+2] dipolar cycloaddition with azides are especially well-suited for use herein due to low toxicity as compared to the metal catalyzed reactions. Examples include DIFO and DIMAC. Reaction of the alkynes and azides is very specific and essentially inert against the chemical environment of biological tissues. One reaction scheme may be represented as:

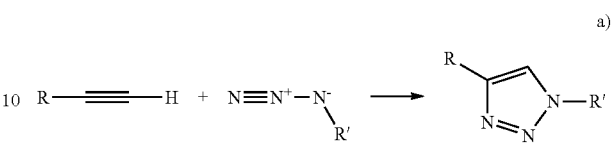

a)

where R and R' are a polymeric material or a component of a biologic tissue.

The Diels-Alder reaction combines a diene (a molecule with two alternating double bonds) and a dienophile (an alkene) to make rings and bicyclic compounds. Examples include:

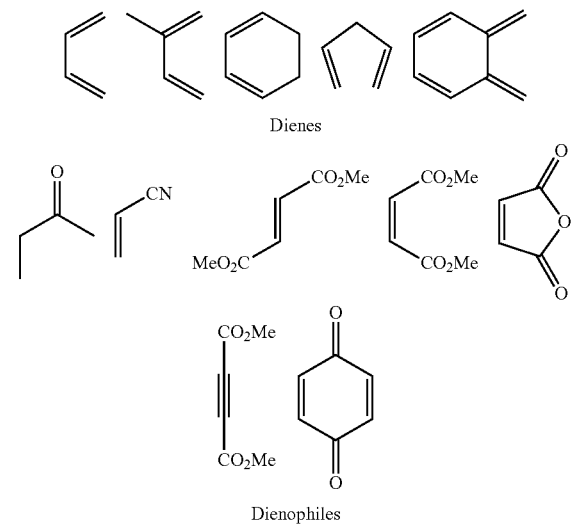

The thiol-alkene (thiol-ene) reaction is a hydrothiolation, i.e., addition of RS—H across a C═C bond. The thiol-ene reaction proceeds via a free-radical chain mechanism. Initiation occurs by radical formation upon UV excitation of a photoinitiator or the thiol itself. Thiol-ene systems form ground state charge transfer complexes and therefore photopolymerize even in the absence of initiators in reasonable polymerization times. However, the addition of UV light increases the speed at which the reaction proceeds. The wavelength of the light can be modulated as needed, depending upon the size and nature of the constituents attached to the thiol or alkene. A general thiol-ene coupling reaction mechanism is represented below:

Initiation

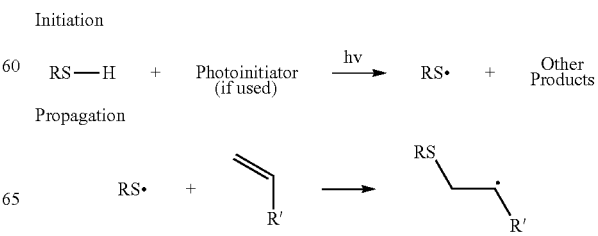

Propagation

-continued

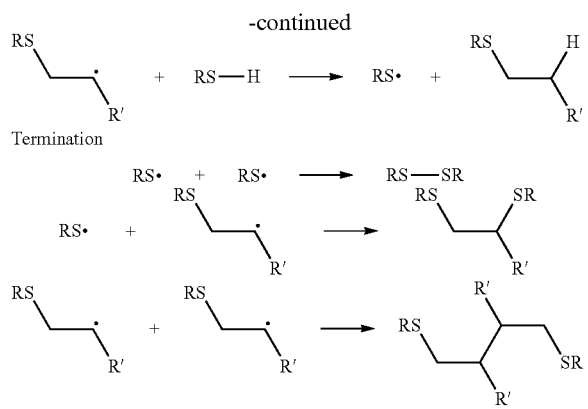

Termination

Thus, suitable reactive members that may be applied to the plasma treated substrate include, for example, an amine, sulfate, thiol, hydroxyl, azide, alkyne, alkene, carboxyl groups aldehyde groups, sulfone groups, vinylsulfone groups, isocyanate groups, acid anhydride groups, epoxide groups, aziridine groups, episulfide groups, groups such as —$CO_2N(COCH_2)_2$, —$CO_2N(COCH_2)_2$, —$CO_2H$, —CHO, —$CHOCH_2$, —N=C=O, —$SO_2CH$=$CH_2$, —$N(COCH_2)_2$, —S—S—($C_5H_4N$) and groups of the following structures wherein X is halogen and R is hydrogen or $C_1$ to $C_4$ alkyl:

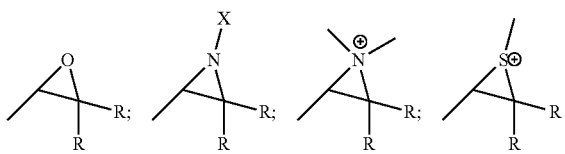

The plasma treated substrate can be provided with click reactive members using any variety of suitable chemical processes. Those skilled in the art reading this disclosure will readily envision chemical reactions for activating plasma treated substrate to render them suitable for use in the presently described devices/methods.

For example, in embodiments, the plasma treated substrate is functionalized with a halogen group to provide a reactive site at which a click reactive member can be attached. The halogenated sites on the surface of the plasma treated substrate can be functionalized with a click reactive member, for example, by converting pendant chlorides on the core into an azide by reacting it with sodium azide. See, R. Riva et al., *Polymer* 49 pages 2023-2028 (2008) for a description of suitable reaction conditions. The halogenated polymer or copolymer backbone may be converted to the alkyne by reacting it with an alcoholic alkyne such as propargyl alcohol. These functionalities may be used to crosslink the substrate or tether drugs, therapeutics, polymers, biomolecules or even cells of interest to the substrate.

Uses of Medical Devices Having an Activated Surface

Medical devices having an activated surface in accordance with the present disclosure can be used for a variety of purposes. For example, in embodiments they may be used for drug delivery. In such embodiments, the drug to be delivered is functionalized with one or more reactive member that are complementary to the reactive members provided on the surface of the substrate. By "complementary" it is meant that the reactive members on the drug to be delivered are able to interact with the reactive members provided on the surface of the substrate to covalently bond the drug to be delivered to the surface activated substrate.

In other embodiments, the medical device having an activated surface in accordance with the present disclosure can be attached to biological tissue by functionalizing tissue with one or more reactive member that are complementary to the reactive members provided on the surface of the substrate. Biological tissue can be provided with reactive member that are complementary to the reactive members provided on the surface of the substrate by conjugation of such groups to various components of tissue such as proteins, lipids, oligosaccharides, oligonucleotides, glycans, including glycosaminoglycans. In embodiments, the complementary groups are attached directly to components of the tissue. In other embodiments, the complementary groups are attached to components of the tissue via a linker. In either case, situating the complementary groups on the tissue can be accomplished by suspending the reactive member in a solution or suspension and applying the solution or suspension to the tissue such that the reactive member binds to a target. The solution or suspension may be poured, sprayed or painted onto the tissue, whereupon the reactive members are incorporated into the tissue.

Those skilled in the art reading this disclosure will readily envision other uses for the activated medical devices described herein.

It will be understood that various modifications may be made to the embodiments disclosed herein. Therefore, the above description should not be construed as limiting, but merely as exemplifications within the scope and spirit of the claims appended hereto.

What is claimed is:

1. A medical device having a plasma-treated surface that is functionalized with a click reactive member to provide an activated surface on the medical device.

2. The medical device of claim 1, wherein the medical device comprises a biodegradable polymer selected from collagen, cellulose, poly (amino acids), polysaccharides, hyaluronic acid, gut, copolymers and combinations thereof.

3. The method of claim 1, wherein the medical device comprises a non-degradable polymer selected from fluorinated polymers, polyolefins, nylons, polyamides, polyurethanes, silicones, ultra high molecular weight polyethylene, polybutesters, polyaryletherketone, copolymers and combinations thereof.

4. The medical device of claim 1, wherein the click reactive member is selected from the group consisting of thiols, azides, alkynes and alkenes.

5. The medical device of claim 1, wherein the click reactive member comprises a thiol.

6. The medical device claim 1, wherein the click reactive member comprises an azide.

7. The medical device of claim 1, wherein the click reactive member comprises an alkyne.

8. The medical device of claim 1, wherein the click reactive member comprises an alkene.

9. The medical device of claim 1, wherein the medical device is selected from the group consisting of monofilament sutures, multifilament sutures, surgical meshes, ligatures, sutures, staples, slings, patches, foams, pellicles, films, barriers, stents, catheters, and inflatable balloons.

10. A method of preparing a medical device having an activated surface, the method comprising:
plasma treating at least a portion of a surface of an absorbable polymeric medical device; and attaching one or more click reactive members to the plasma treated surface of the absorbable polymeric medical device.

11. The method according to claim 10, wherein the plasma treating provides reactive members on the surface of the medical device.

12. The method according to claim 10, wherein the plasma treating provides a coating on the device, the coating including reactive members on the surface of the medical device.

13. The method according to claim 10, wherein the medical device comprises a natural polymer selected from collagen, cellulose, poly (amino acids), polysaccharides, hyaluronic acid, gut, copolymers and combinations thereof.

14. The method according to claim 10, wherein the click reactive member is selected from the group consisting of thiols, azides, alkynes and alkenes.

15. The method according to claim 10, wherein the click reactive member comprises a thiol.

16. The method according to claim 10, wherein the click reactive member comprises an azide.

17. The method according to claim 10, wherein the click reactive member comprises an alkyne.

18. The method according to claim 10, wherein the click reactive member comprises an alkene.

19. The method according to claim 10, wherein the medical device is selected from the group consisting of monofilament sutures, multifilament sutures, surgical meshes, ligatures, sutures, staples, slings, patches, foams, pellicles, films, barriers, stents, catheters, and inflatable balloons.

20. The method according to claim 10, wherein the medical device comprises a synthetic polymer.

21. The method according to claim 10 wherein the plasma treatment lasts less than 5 minutes.

22. The method according to claim 10 further comprising the step of combining the absorbable polymeric medical device with a drug functionalized with one or more complimentary click reactive members to covalently bond the drug to the surface of the absorbable polymeric substrate for drug delivery.

* * * * *